(12) United States Patent
Ioannidis et al.

(10) Patent No.: US 9,050,159 B2
(45) Date of Patent: Jun. 9, 2015

(54) PERIODONTAL PROBE WITH TOUCH SENSING

(71) Applicants: Nektarios Ioannidis, London (CA); Demetrios Argyrios Margaritis, London (CA)

(72) Inventors: Nektarios Ioannidis, London (CA); Demetrios Argyrios Margaritis, London (CA)

(73) Assignees: Nektarios Ioannidis, Ontario (CA); Demetrios Argyrios Margaritis, Ontario (CA)

( * ) Notice: Subject to any disclaimer, the term of this patent is extended or adjusted under 35 U.S.C. 154(b) by 44 days.

(21) Appl. No.: 13/709,457

(22) Filed: Dec. 10, 2012

(65) Prior Publication Data

US 2014/0120492 A1 May 1, 2014

(30) Foreign Application Priority Data

Oct. 31, 2012 (CA) .................................... 2794231

(51) Int. Cl.
*A61C 19/04* (2006.01)
(52) U.S. Cl.
CPC .................................... *A61C 19/043* (2013.01)
(58) Field of Classification Search
CPC ...................................................... A61C 19/043
USPC .................................................... 433/27, 224
See application file for complete search history.

(56) References Cited

U.S. PATENT DOCUMENTS

| | | | |
|---|---|---|---|
| 4,177,799 A * | 12/1979 | Masreliez | 600/554 |
| 4,417,140 A | 11/1983 | Adolfsson et al. | |
| 4,501,555 A * | 2/1985 | Ditchburn | 433/29 |
| 4,708,647 A | 11/1987 | Pippin et al. | |
| 4,791,940 A | 12/1988 | Hirschfield et al. | |
| 4,883,425 A * | 11/1989 | Zimble | 433/32 |
| 4,962,765 A | 10/1990 | Kung et al. | |
| 4,995,403 A | 2/1991 | Beckman et al. | |
| 5,022,856 A * | 6/1991 | Zimble | 433/72 |
| 5,112,226 A * | 5/1992 | Lemon et al. | 433/72 |
| 5,244,387 A | 9/1993 | Fuierer | |
| 5,423,677 A * | 6/1995 | Brattesani | 433/72 |
| 5,725,373 A * | 3/1998 | Yeh | 433/72 |
| 5,993,209 A | 11/1999 | Matoba et al. | |
| 5,997,296 A * | 12/1999 | Schuldink | 433/72 |
| 6,179,611 B1 * | 1/2001 | Everett et al. | 433/29 |
| 2002/0133096 A1 | 9/2002 | Toda et al. | |
| 2004/0249268 A1* | 12/2004 | Da Silva | 600/424 |
| 2006/0257820 A1* | 11/2006 | Davis | 433/141 |
| 2007/0196784 A1* | 8/2007 | Bochi | 433/114 |
| 2010/0239996 A1* | 9/2010 | Ertl | 433/29 |

FOREIGN PATENT DOCUMENTS

| | | |
|---|---|---|
| EP | 2165674 | 3/2010 |
| JP | 1998-005254 | 1/1998 |
| JP | 1998-118102 | 5/1998 |

(Continued)

*Primary Examiner* — Cris L Rodriguez
*Assistant Examiner* — Hao D Mai
(74) *Attorney, Agent, or Firm* — Adam K. Sacharoff; Much Shelist

(57) ABSTRACT

A periodontal probe is provided for measuring a depth of a periodontal pocket using a touch sensor. The periodontal probe includes a handle with a probe tip for insertion into the periodontal pocket. The probe tip includes a touch sensitive reader located on or near an exterior surface thereof for measuring contact between the exterior surface of the probe tip and the tissue of the periodontal pocket. A touch sensor and a microcontroller are connected to the touch sensitive reader to measure the amount of contact between the touch sensitive reader and the tissue of the periodontal pocket, which corresponds to the depth of the periodontal pocket.

8 Claims, 10 Drawing Sheets

(56) References Cited

FOREIGN PATENT DOCUMENTS

| JP | 1998-165425 | 6/1998 |
| JP | 2007-152004 | 6/2007 |
| WO | 84/03143 | 8/1984 |
| WO | 89/01314 | 2/1989 |

* cited by examiner

PERIODONTAL PROBE WITH TOUCH SENSING

FIELD

This invention relates to the field of dentistry, specifically the periodontal diagnostic area. In particular, this invention relates to a periodontal probe having an electronic recording capability, which accurately measures and records the depth of the periodontal pocket surrounding a tooth.

BACKGROUND

In the dental field periodontal disease is known to be a progressive, plaque-induced disease. Periodontal disease can cause serious tissue inflammation and even bone loss in the areas surrounding the teeth of those afflicted. To effectively treat periodontal disease it is essential to monitor the progression of the disease in the mouths of patients. To monitor the progression of periodontal disease a dental professional periodically measures the depths of the periodontal pockets surrounding the teeth.

The periodontal pocket is the physical distance from the top of the gingival tissue surrounding a tooth, to the depth that a probe will physically extend, until contact pressure impedes the probe from entering the pocket any further. This is usually at the level where the epithelial attachment starts between the gum and tooth root. As periodontal changes occur, the relative depth of the periodontal pocket increases. Measurements are usually taken in millimeters.

In the dental setting, accurately and thoroughly measuring the peridontium can be time consuming and tedious. Conventional probing, still utilized by most dental offices, requires the operator to stop and record the depth of the periodontal pocket at least after the measurement of every tooth, or an assistant is required to record the measurements. Traditionally, the measurements are manually written on the patient's chart. The process of measuring and recording is repeated for each periodontal pocket to be measured.

Conventional probes have lines, marks or colours to indicate the depth that the probe penetrates into the pocket between the tooth and the gum. The dental professional has to manually read the depth of the probe. Probes are small and such readings are difficult to make accurately. Very small differences can be important in monitoring the progression of periodontal disease. There is also a problem of subjectivity. Different dental professionals may have different techniques or may view the periodontal probe at a different angle when taking measurements on different days. Different measurement techniques are a significant problem in offices with multiple hygienists or dentists, as each practitioner could employ a different measuring technique for the same patient during different visits.

Aside from conventional graduated probes, many instruments exist to measure the depth of the periodontal pocket. One of these devices is the electronic periodontal probe with a constant force applier, also known by the trademark FLORIDA PROBE™, which is described in U.S. Pat. No. 4,791,940, and Canadian Patent No. 1,282,236 to Hirschfeld et al. This probe and recording apparatus uses a spring tension device electronically connected by a transducer to the recording apparatus. The probe tip, attached to a movable or mechanical arm, moves within a narrow sleeve fixed to a probe handle. When the probe tip rests at the bottom of the pocket, the probe handle is pressed until the sleeve end touches the gingival margin. The subsequent exposed length above the sleeve represents the depth of the pocket. A foot switch triggers electronic measurement from the mechanical displacement of the transducer to the recording apparatus. This probe has several disadvantages. First, the mechanical moving parts in the narrow sleeve, arm, handle and spring are all subject to loss of integrity that may change the consistency of the force required to allow spring tension transduction. Second, the probe tip needs to be removed for sterilization. Third, the height from probe tip to the top of the mechanical moving arm may make it difficult to obtain readings in the back of the mouth where there is less room. Furthermore, the size may make it difficult to get proper readings in patients with limited opening ability.

U.S. Pat. No. 4,995,403 to Beckman et al. describes a periodontal probe with a retractable fiber element for measuring. Again, there are movable parts that are subject to frictional inaccuracies in measurement. Also, a large portion of the instrument is not sterilizable and needs to be disposed of, making the overall length of the device substantial. The large length can create issues in positioning the probe for measuring and can be cumbersome and uncomfortable for a dental professional to use.

Another example of a movable sleeve and tip is described in U.S. Pat. No. 5,993,209 to Matoba et al. This device detects positional differences between the tip of the probe and the tip of the sleeve when the tip of the probe is inserted into the bottom of the pocket and the sleeve is at the top of the gingiva. Again, movable parts are a disadvantage and all the components comprising the apparatus that move could add to inaccuracies due to friction during movement of the probe within the sleeve, at the elbow, or along the terminal sleeve.

In the past, to reduce time and produce consistency with periodontal probing examinations, attempts have been made to produce periodontal probes that will electronically record the depth of periodontal pockets. One disadvantage of these probes is that they have movable parts that can lead to difficulties with sterilization, and inconsistency in the overall measurements. Moreover, these probes tend to be large and bulky.

The prior art lacks probes that can quickly and easily determine the depth of the periodontal pocket by measuring the amount of marginal tissue without relying on the dental professional's technique. The prior art also lacks a probe that compiles electronic measurements, is lightweight, provides consistent accuracy, and is easy to sterilize.

SUMMARY

The present periodontal probe with touch sensing addresses the major shortcomings of the prior art.

The present periodontal probe described herein seeks to provide a probe that can quickly and accurately measure and record the depth of a patient's periodontal pockets. The present periodontal probe seeks to eliminate operator subjectivity when taking measurements and seeks to eliminate possible inaccuracies that may occur as a result of having moving parts. The periodontal probe described herein seeks to reduce significantly the amount time required for recording measurements, and to eliminate operator subjectivity when reading the probe markings.

It is an aspect of the periodontal probe described herein to provide a probe that accurately and quickly measures a patient's periodontal pockets using a touch sensor. The marginal tissue of the gingival will cause an electronic signal to be produced that relates to the depth to which the periodontal probe has been inserted into the periodontal pocket.

A further aspect relates to a periodontal probe with a touch sensor that in communication with a computer. The computer records the different depths of the patient's periodontal pockets.

Another aspect relates to a periodontal probe that has no moving parts, and can be sterilized without the possibility of misalignment of any moving parts due to temperature cycling.

In accordance with one aspect then, there is provided a periodontal probe for measuring a depth of a periodontal pocket, the periodontal probe comprising: a handle; a probe tip having a proximal end connected to the handle and an opposite distal end for insertion into the periodontal pocket, the probe tip including a touch sensitive reader for measuring contact between an exterior surface of the probe tip and tissue comprising the periodontal pocket; and a touch sensor and a microcontroller connected to the touch sensitive reader for measuring an amount of the contact between the exterior surface of the probe tip and the tissue of the periodontal pocket; wherein the amount of the contact between the exterior surface of the probe tip and the tissue of the periodontal pocket corresponds to the depth of the periodontal pocket.

In accordance with another aspect, there is provided a method for using the periodontal probe described above, comprising inserting the distal end of the probe tip into the periodontal pocket until the distal end of the probe tip contacts a bottom of the periodontal pocket and the exterior surface of the periodontal probe makes contact with the tissue of the periodontal pocket.

BRIEF DESCRIPTION OF THE DRAWINGS

Referring to the drawings wherein like reference numerals indicate similar parts throughout the several views, several aspects of the periodontal probe with touch sensing are illustrated by way of example, and not by way of limitation, in detail in the figures, wherein.

DETAILED DESCRIPTION

Various embodiments of the applicant's periodontal probe with touch sensing will now be discussed in detail.

Figure 1:
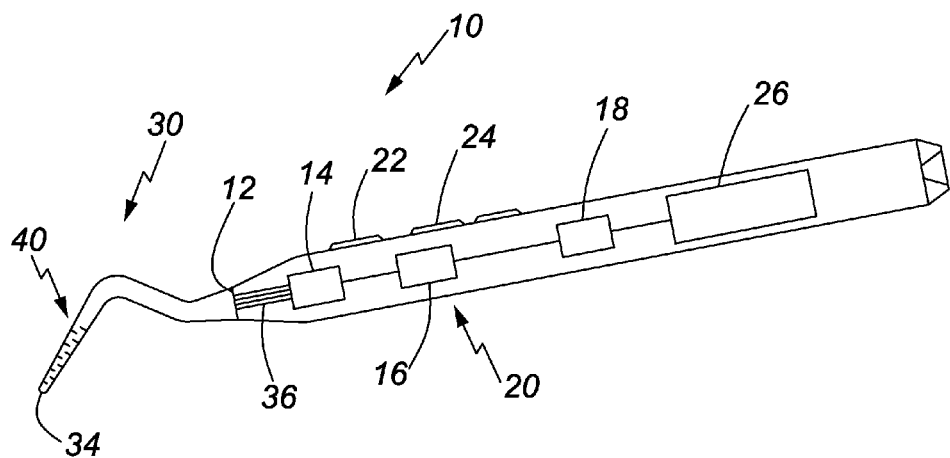
FIG. 1 is a partial cutaway side view of a wireless version of the present periodontal probe.
Figure 2:
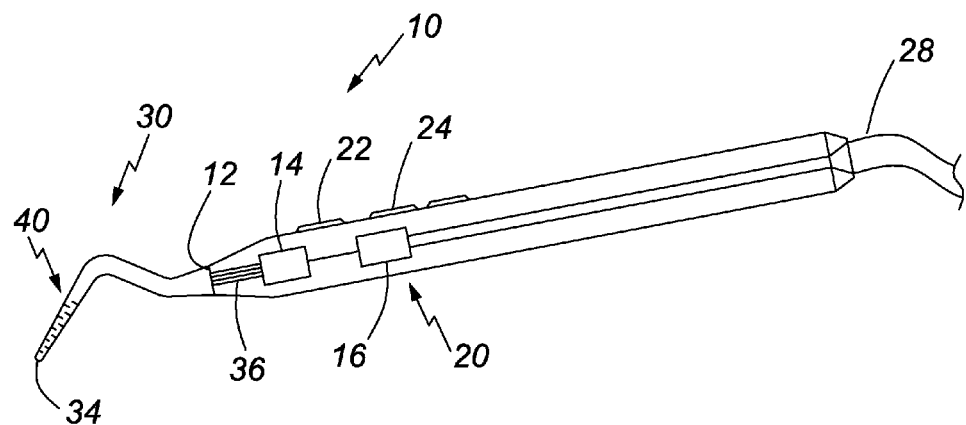
FIG. 2 is a partial cutaway side view of the present periodontal probe periodontal for wired connection to a computer.

FIG. 1 shows a cutaway side view of a periodontal probe 10 comprising a handle 20 and a probe tip 30. The handle 20 is substantially hollow and longitudinally extending. The periodontal probe tip 30 extends from a distal tip end 34, which is inserted into the periodontal pocket, to a proximal end 12 for connection to the handle 20. The probe tip 30 may include a bend at about 15-20 millimeters from the tip end 34, forming a probe elbow 32. The probe tip 30 may be tapered toward the tip end 34 and the tip end 34 may be rounded. The probe tip 30 may be hollowed throughout its length to allow insulated wires 36 (see FIG. 4) to travel through from the probe tip 30 to the handle 20. Probe tip 30 may also include traditional increment markings on the outside surface as shown in FIGS. 1 and 2.

The entire periodontal probe 10, including probe tip 30, and handle 20, is preferably made of a material that can be sterilized, namely a plastic, or lightweight, non-corrosive metal, and has no moving parts. This advantageously allows the entire probe 10 to be sterilized. In the alternative, the periodontal probe 10 may have a detachable interface where tip 30 connects to handle 20 at the proximal end 12. The connection at proximal end 12 may be a snap or a twist connection, although other suitable connections are envisioned. This allows the probe tip 30 to be removed from handle 20 and sterilized or disposed. Alternatively, probe tip 30 may be permanently attached to handle 20.

The probe tip 30 includes a touch sensitive reader 40 located on or near the exterior surface of the probe tip 30 that is in communication with a touch sensor 14, that is in turn in communication with a microcontroller 16. The touch sensor 14 may be located in the handle 20 or elsewhere. The touch sensitive reader 40 measures physical contact between the exterior surface of the probe tip 30 and the human tissue comprising the periodontal pocket. The amount of the contact between the exterior surface of the probe tip 30 and the tissue of the periodontal pocket is determined by the touch sensor 14 and the microcontroller 16 and corresponds to the depth of the periodontal pocket.

The handle 20 may also contain an activation button 22, a display 24 and a rechargeable battery 26. In one embodiment, the handle 20 also houses a wireless receiver/transmitter 18 (see FIG. 1). Alternatively, the handle 20 may be hard-wired to a computer through a wire 28 (see FIG. 2). In this embodiment, the handle would not require a receiver/transmitter or a battery. The activation button 22 is preferably located so that it may be easily pressed by the operator. When the activation button 22 is pressed, a signal is sent to the microcontroller 16 to take a reading and record the current input state of the touch sensor 14.

As will be explained in greater detail below, the touch sensor 14 receives electric signals from the touch reader 40 and sends these readings to the microcontroller 16, which converts the readings into a numerical depth measurement of the periodontal pocket. The display 24 may be used to display the measurement. The rechargeable battery 26 is used to supply power to the components of the periodontal probe, including the touch sensor 14, the microcontroller 16 and the wireless receiver/transmitter 18. If the periodontal probe 10 is hard-wired to a computer the power necessary to run these components may be delivered through the wire 28.

The microcontroller 16 may also be configured to detect operator input from secondary buttons for any other user features that may be included in the present periodontal probe, such as skipping a tooth, adjusting pressure sensitivity for recording, and control of a possible light source (not shown) to improve visibility.

Probe tip 30 may be pivotal with respect to handle 20 at the proximal end connection point 12. This would allow the probe tip 30 to be rotated at varying angles relative to the handle 20, to permit taking measurements in areas that may be difficult to otherwise access.

Figure 3:
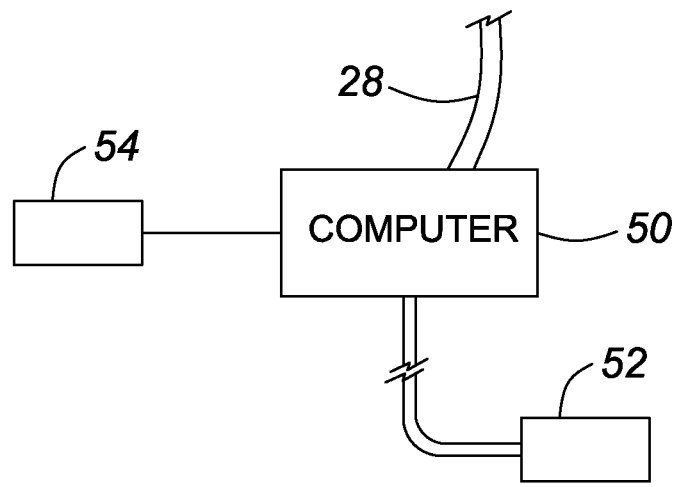
FIG. 3 is a schematic view of a computer used to connect to the present periodontal probe.

FIG. 3 is a schematic diagram showing a computer 50, which may be used to receive and record information regarding the depth of the periodontal pocket from the microcontroller 16. Computer 50 is in communication with the periodontal probe 10, either via a wireless receiver/transmitter 54 for receiving and transmitting wireless signals from and to the wireless transmitter/receiver 18, or by being directly connected to the periodontal probe 10 by wire 28. Computer 50 may be attached to a foot pedal 52 that can be used to activate the periodontal probe 10 for taking a measurement reading.

Figure 4:
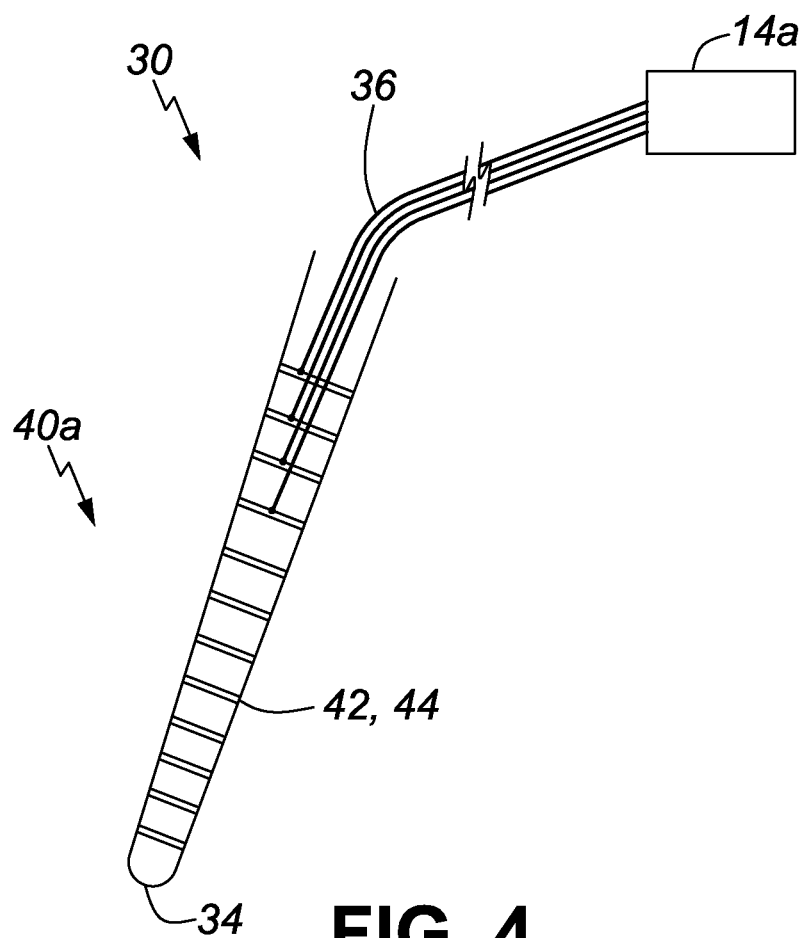
FIG. 4 is a cutaway side view of a probe tip of the present periodontal probe having one embodiment of a capacitive touch reader.

In one embodiment, as shown in FIG. 4, the touch sensitive reader 40 is a capacitive touch reader 40*a* and the touch sensor 14 is a capacitive touch sensor 14*a*. The capacitive touch sensor 14*a* is comprised of one or more individual capacitive touch sensing circuits (not shown), each individual sensing circuit being connected to an individual insulated wire 36. In this description, the individual capacitive touch sensing circuits and the collective capacitive touch sensor are referred to using reference number 14*a*. An example of one such capacitive touch sensor that may be used is Texas Instruments™ MSP430G2452. The specific capacitance measurement methodology to be used may vary and could be oscillator-based measurement or resistor-based measurement, or any other suitable methodology that will be familiar to those skilled in the art.

Figure 5A:
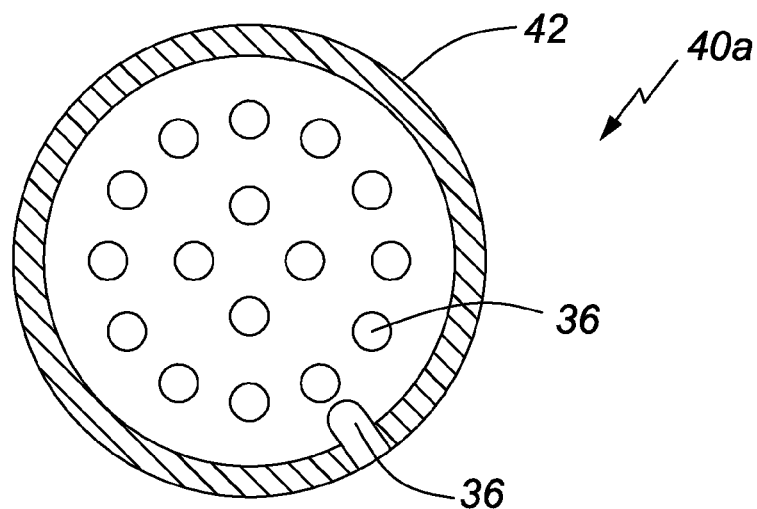
FIGS. 5a and 5b are cross sectional views of periodontal probe tips having the capacitive touch reader shown in FIG. 4.

FIG. 4 illustrates an enlarged cutaway side view of the probe tip 30 of the periodontal probe 10. The tip 30 includes capacitive touch reader 40*a*, which in this embodiment includes of a plurality of thin electrically conductive bands 42, or wire rings 44, placed at one-millimeter increments along the length of the probe tip 30 as shown. The number of conductive bands 42 or wire rings 44 may be varied from one to preferably at least 8 to 10. Each band 42 or wire ring 44 is attached by a selected individual insulated wire 36, to a corresponding individual capacitive sensor circuit 14*a*. In FIG. 4, only four of the bands or wire rings are shown as being connected with wires 36 to sensor circuit 14*a*. These conductive bands 42 or wire rings 44 comprise the capacitive sensor elements for the capacitive touch sensor 14*a* and represent the location where the capacitance reading is taken. FIG. 5A is a cross section of the probe tip 30 taken at the location of one of the conductive bands 42 shown in FIG. 4. One of the insulated wires 36 is shown connecting to the band 42.

Figure 5B:
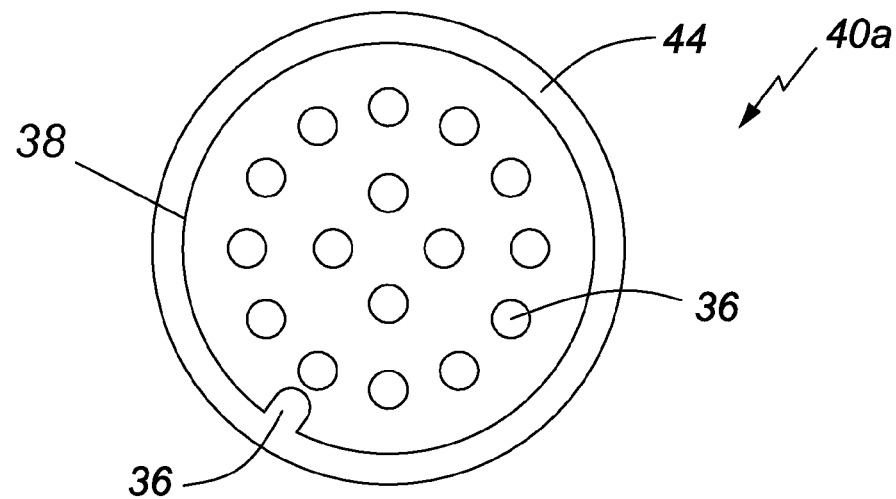

In an alternative arrangement shown in FIG. 5B, the electrically conductive bands 42 on probe tip 30 are replaced by wire rings 44. Each insulated wire 36 exits onto the outer surface 38 of the probe tip 30, and forms a conductive wire ring 44 that wraps around the probe tip 30.

Each insulated wire 36 extends upwards through the shaft of the periodontal probe tip 30, along the probe elbow 32, and attaches to a separate capacitive sensor circuit 14*a*, which is in turn connected to microcontroller 16. A capacitance reading on each band 42 or wire ring 44 is measured by the corresponding capacitive sensor circuit 14*a* and sent to the microcontroller 16. Capacitive sensor circuit 14*a* is constantly monitoring the capacitance of the conductive wire band 42 or ring 44. Each wire band 42 or ring 44 has a base capacitance reading when not in contact with tissue. When the conductive band 42 or wire 44, comes in contact with tissue in the periodontal pocket, the capacitance reading of the corresponding capacitive touch sensor circuit 14*a* will change. Once the change in capacitance reaches a pre-determined threshold, determined by the type of tissue, moistness and salt content, the sensor circuit 14*a* will register a reading. The location of the change in capacitance above the pre-determined threshold is detected by determining which wire band 42 or ring 44 has been triggered. This location is translated into a corresponding depth measurement in millimeters by the microcontroller 16. For example, when the probe tip 30 is not in contact with tissue, all of the insulated wires 36 will transmit the same base capacitance reading to their corresponding capacitive touch sensor circuit 14*a*. As the probe tip 30 is inserted into the periodontal pocket, successive bands 42 or wire rings 44 will come into contact with tissue surrounding the pocket, commencing from the probe tip end 34 upward toward the probe elbow 32. The contact with tissue will cause a change in capacitance reading from each successive corresponding capacitive sensor circuit 14*a*. The number of bands 44 or wire rings 42 for which the capacitance reading changes above a pre-determined threshold will correspond in millimeters to the depth of the periodontal pocket.

Figure 6:
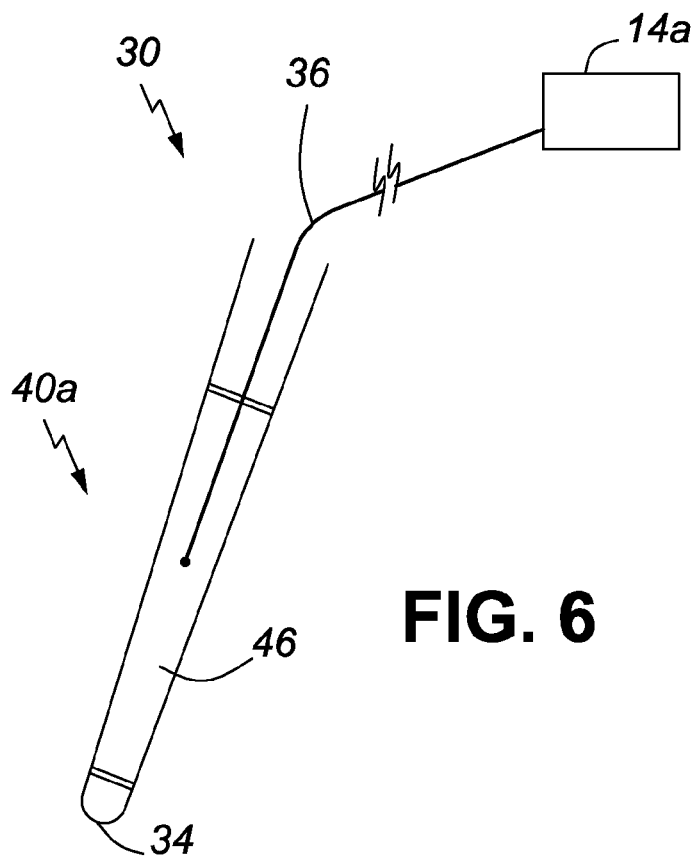
FIG. 6 is a cutaway side view of a probe tip having a capacitive touch reader with a single conductive band.

FIG. 6, shows an alternative arrangement where the capacitive touch reader 40*a* comprises a single conductive band 46. In this arrangement, capacitive touch sensor 14*a* is configured to provide a quantitative reading of the capacitance of the conductive band 46, rather than to detect a change in capacitance above a certain threshold. As the probe tip 30 is inserted into the periodontal pocket contact is made between the exterior surface of the probe tip 30 and the moist tissue, which creates a specific capacitance reading on band 46. As the probe tip 30 is inserted further into the periodontal pocket, the capacitance reading increases due to increased contact between the probe tip 30 and the tissue of the periodontal pocket. The increase in capacitance of the band 46 corresponds to the amount of tissue that has come into contact with the exterior surface of probe tip 30, which corresponds to the depth of the periodontal pocket.

Figure 7:
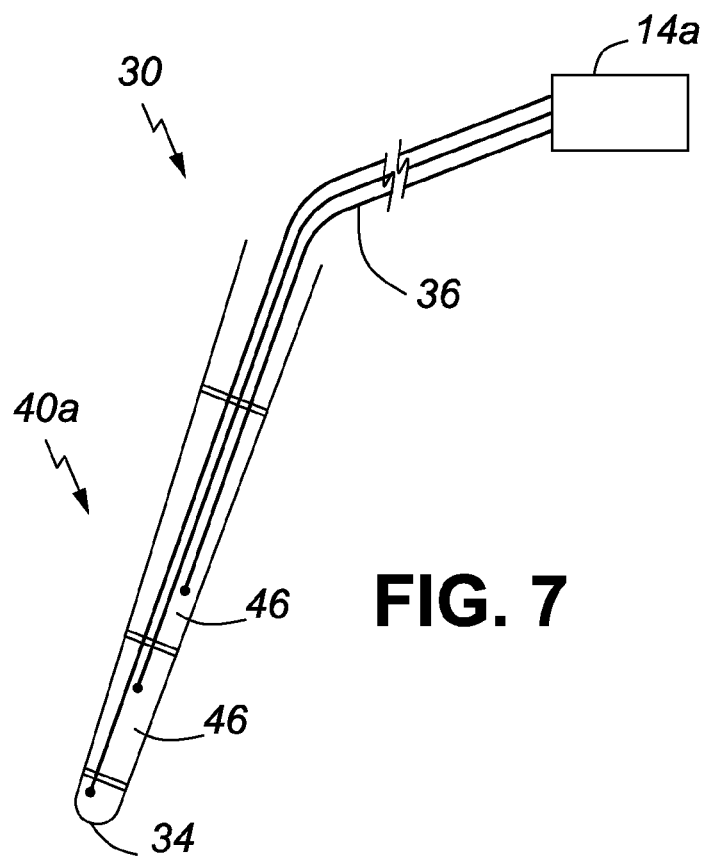
FIG. 7 is a cutaway side view of a probe tip having a capacitive touch reader with variable sized conductive bands.

As shown in FIG. 7, there may be multiple conductive bands 46 of equal or unequal width, each separated by an insulating ring. FIG. 7 shows three bands 46, each connected to a separate capacitive touch sensor circuit 14*a*.

Figure 8:
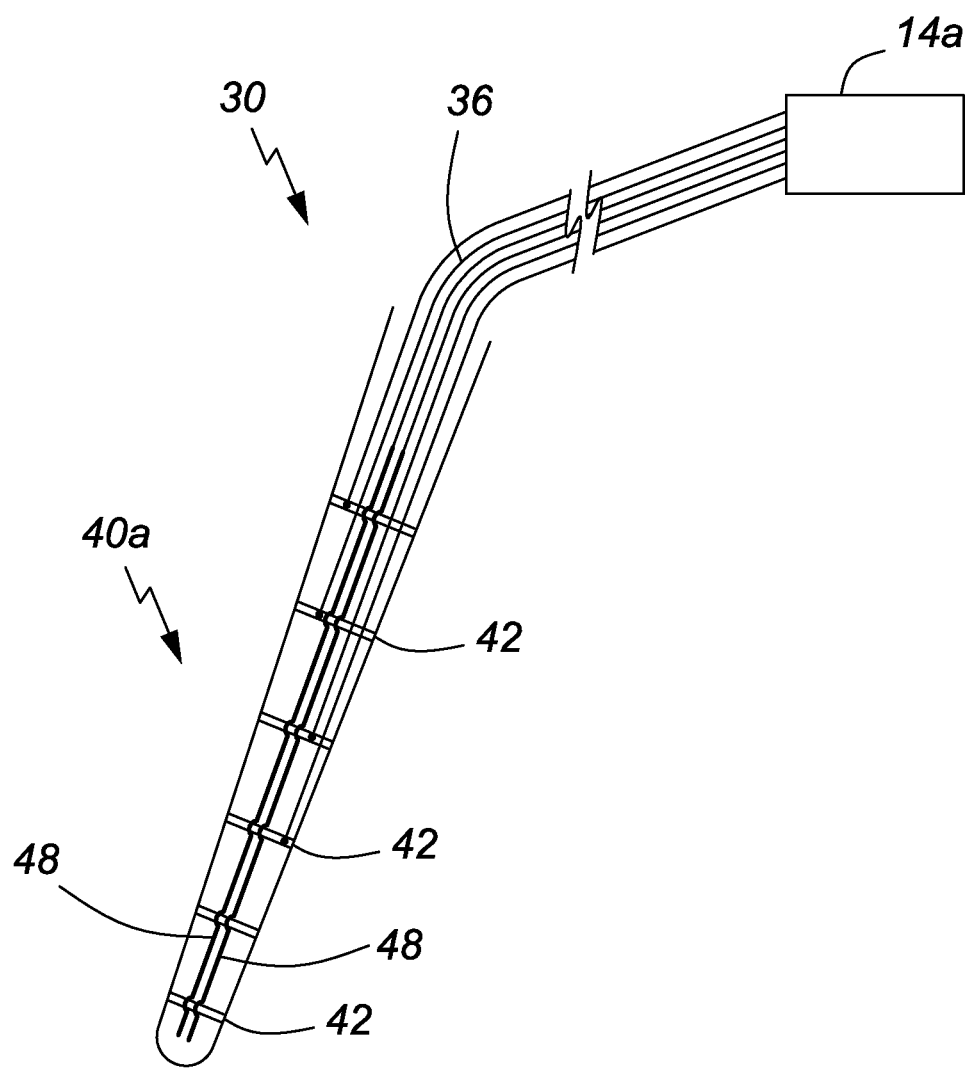
FIG. 8 is a cutaway side view of a probe tip having a capacitive touch reader arranged in a grid pattern.

FIG. 8, shows a further alternative arrangement, where the capacitive touch reader 40*a* comprises a wire grid formed by one or more conductive wire rings 42 that wrap around the outside circumference of probe tip 30 and one or more conductive wire strips 48 that run longitudinally on the outside surface of the probe tip 30. The wire rings 42 are electrically insulated from the wire strips 48. Each of the wire rings and wire strips is connected to a separate capacitive touch sensor circuit 14*a* by wires 36 and comprise the capacitive sensor element for that sensor circuit. In FIG. 8, only two of the multiple wire strips making up the grid are illustrated, and only four of the wire rings are shown as being connected by wires 36. In this arrangement, capacitive touch sensor 14a is configured to provide a detailed pattern of capacitance readings at various locations circumferentially around and longitudinally along the exterior surface of probe tip 30. In this way, more detailed information can be provided, such as the depth, shape and the three-dimensional structural integrity of the periodontal pocket.

One method of using the periodontal probe shown in FIG. 4 is for the operator to grip the periodontal probe 10 by the probe handle 20. The probe tip 30 is inserted into the periodontal pocket, in the area between the gingival margins and the tooth root. The probe tip 30 is gently guided into the periodontal pocket until resistance is met at the base of the pocket. Tissue surrounding the periodontal pocket comes in contact with the outside surface of the probe tip 30. At this time, the operator depresses the activation button 22 on the probe handle 20 or depresses the foot pedal 52, thereby signaling the microprocessor 16 to take a reading. The microprocessor 16 records the amount of contact between the exterior surface of the probe tip 30 and the tissue of the periodontal pocket by measuring the changed capacitance readings, above a pre-determined threshold, from the individual capacitive sensor circuits 14a, thus registering how many millimeters of the probe tip 30 has been inserted into the periodontal pocket. This depth information is then displayed on the display 24. The depth information may also be sent to the computer 50 where it may be displayed, processed by software and recorded. The information can be used to keep records of patient history for assessing and keeping track of the patient's periodontal health.

The periodontal probes shown in FIGS. 6 and 7 work in the same way, except that when a capacitance reading is taken a quantitative value of capacitance above the base capacitance is obtained, which correlates to the amount of tissue that is in contact with the exterior surface of probe tip 30, which in turn corresponds to the depth the probe tip 30 has been inserted into the periodontal pocket.

Figure 9:
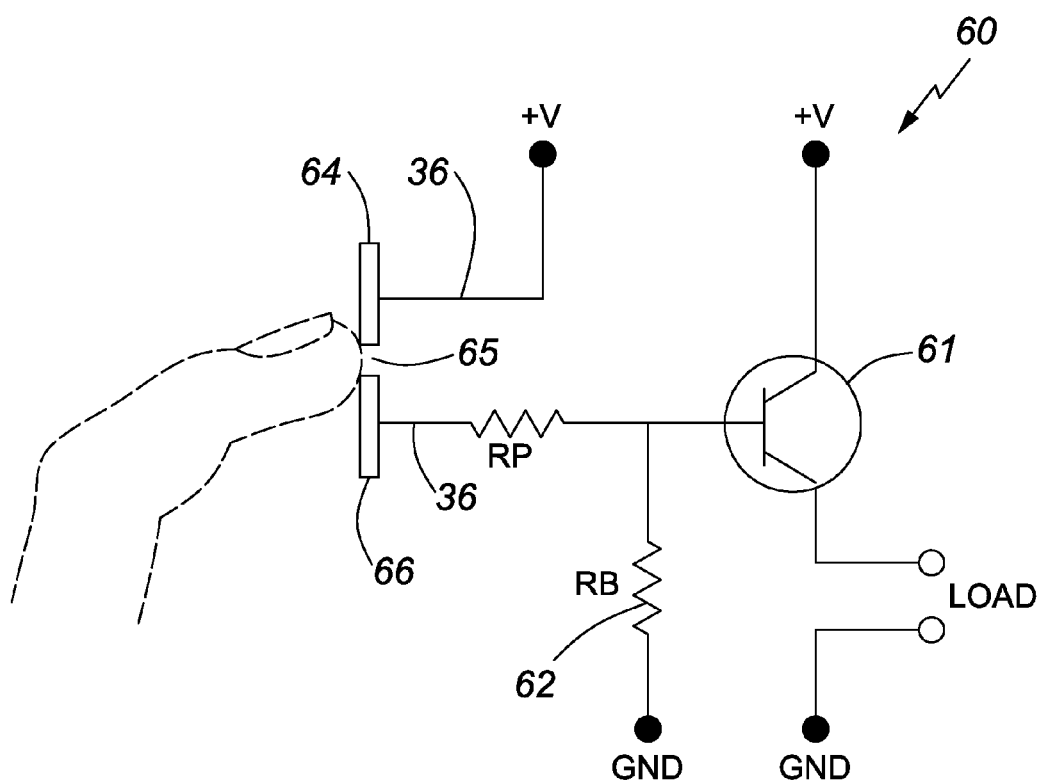
FIG. 9 shows one example of a circuit for a resistance touch reader for the present periodontal probe.
Figure 10:
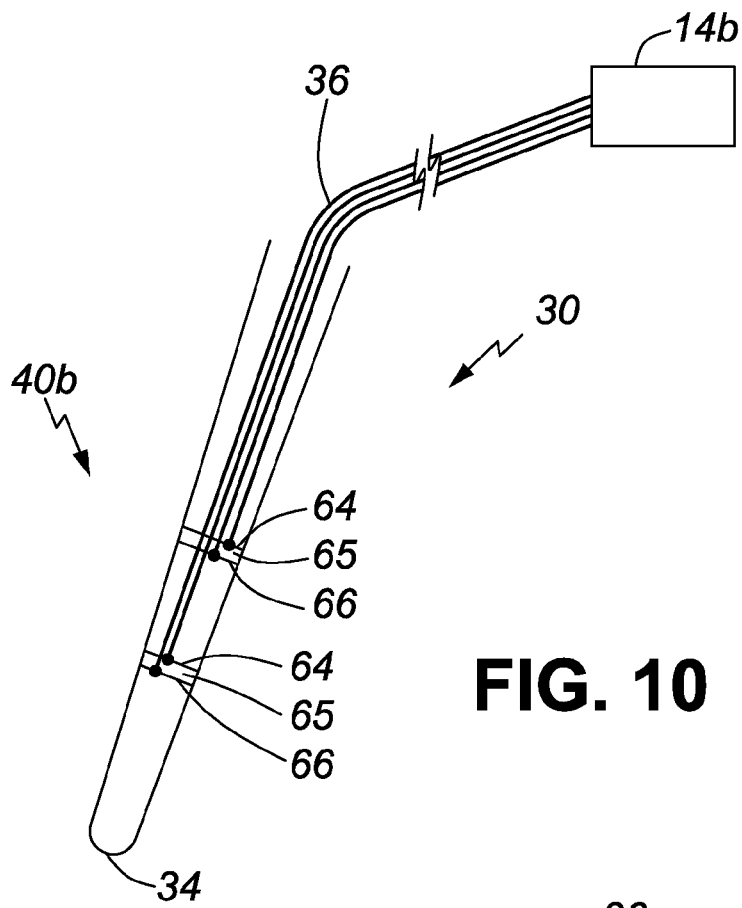
FIG. 10 shows a cutaway side view of a probe tip having one version of a resistance touch reader.
Figure 11:
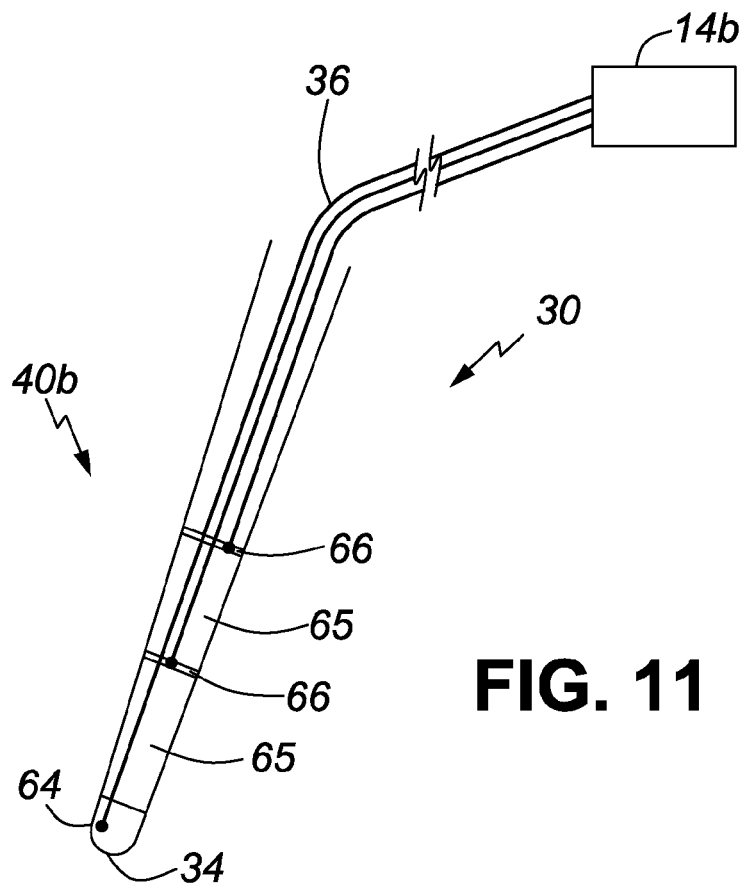
FIG. 11 shows a cutaway side view of a probe tip having another version of a resistance touch reader.
Figure 12:
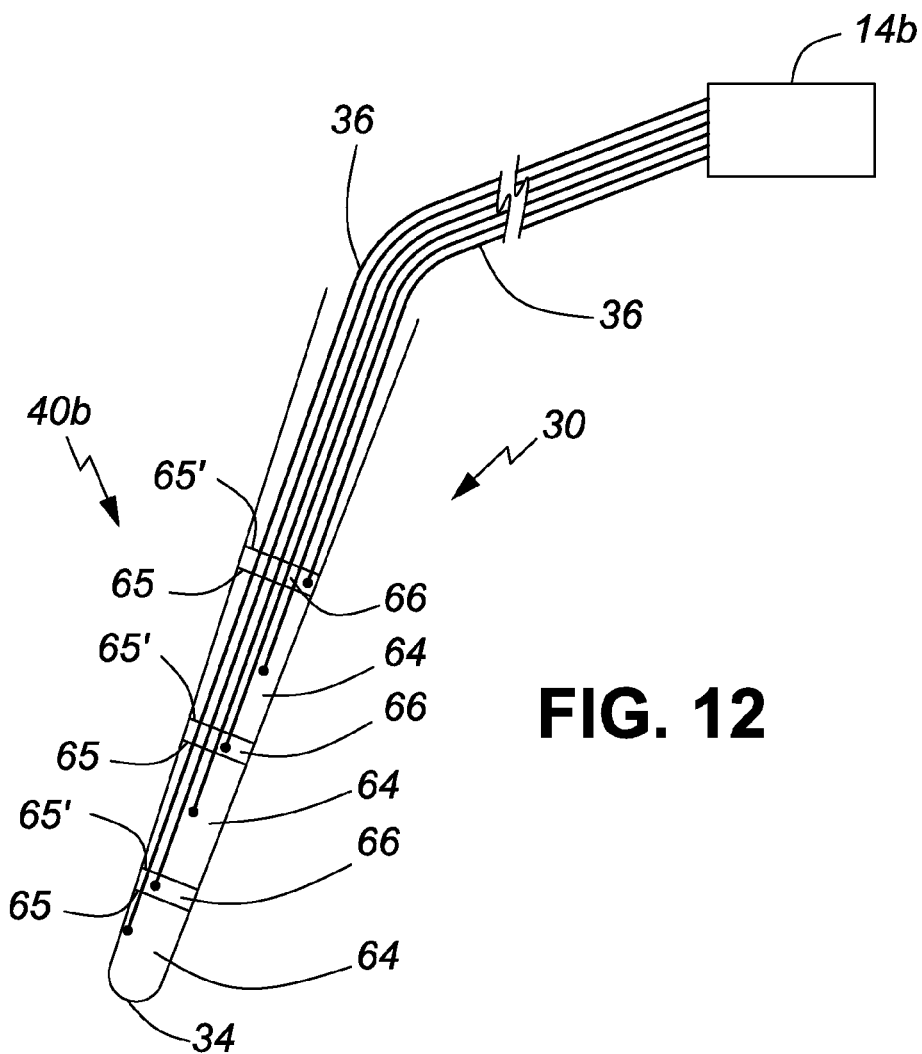
FIG. 12 shows a cutaway side view of a probe tip having yet another version of a resistance touch reader.

In another embodiment, as shown in FIGS. 10-12, the touch reader 40 is a resistance touch reader 40b and the touch sensor 14 is a resistance touch sensor 14b. The resistance touch sensor 14b is comprised of one or more individual resistance touch sensing circuits 60, like the one shown in FIG. 9, which illustrates a basic resistance touch switch. A resistance touch switch is based on the fact that human tissue (like the skin) contains a great amount of water and salt, which makes it conductive. In the sample resistance touch circuit 60 shown in FIG. 9, a transistor 61 is used as a switch. A resister 62 is provided to protect the transistor from an over-current situation in the event of a short circuit. Conductive electrodes 64 and 66 are included in the circuit 60, separated by an insulating gap 65. If one of the electrodes 66, 64 is touched, nothing happens. However, if both electrodes 64 and 66 are touched in such a manner that the insulating gap 65 is bypassed, as shown in FIG. 9, human skin acts like a resister and a slight amount of current will flow between electrodes 64 and 66 and to the base of transistor 61. The state of transistor 61 will change from cut-off to saturation, and current will flow to the LOAD, thus triggering the sensor. Those skilled in the art will appreciate that many other configurations of resistance touch circuit 60 are possible.

FIG. 10 illustrates one example of periodontal probe tip 30 with a resistance touch reader 40b. Pairs of conductive bands or wires 64, 66 located on or near the outer surface of probe tip 30 correspond to electrodes 64, 66 in resistance touch sensing circuit 60 of resistance touch sensor 14b, and are separated by an insulating gap 65. Wires 36 connect the electrodes 64, 66 to resistance touch sensor 14b. When the probe tip 30 is inserted into the periodontal pocket, the surrounding tissue will come in contact with the outside surface of the probe tip 30. If the tissue bridges the insulated gap 65 between conductive bands 64, 66, the corresponding resistance touch sensing circuit 60 will record a positive reading. When the operator depresses the activation button 22 on the probe handle 20 or depresses foot pedal 52, the microprocessor 16 records how many of the sensing circuits 60 have been triggered, thus registering the amount of contact between the exterior surface of the probe tip 30 and the tissue of the periodontal pocket, thereby measuring how many millimeters the probe tip 30 has been inserted into the periodontal pocket. The depth information may be displayed on the display 24 and/or sent to the computer 50.

FIG. 11 illustrates another example of a periodontal probe tip 30 having a resistance touch reader 40b configured in a slightly different manner. In this example, probe distal tip end 34 functions as one of the electrodes 64 in all of the resistance touch sensing circuits 60 of resistance touch sensor 14b. Conductive bands 66 function as the second electrode. The two conductive bands/electrodes 64 and 66 are separated by insulated, non-conducting gaps 65. Wires 36 connect the tip end 34 and conductive bands 66 to resistance touch sensors 14b. The wire 36 connecting tip end 34 is shared by all of the touch sensing circuits 60 of resistance touch sensor 14b. When the probe tip 30 is inserted into the periodontal pocket, the surrounding tissue will come in contact with the outside surface of the probe tip 30. If the tissue bridges the insulated gaps 65 between conductive tip end 34 and conductive bands 66, the corresponding resistance touch sensing circuit 60 will record a positive reading. As the tissue bridges each successive gap 65 to the next conductive band 66, the next corresponding sensing circuit 60 will record a positive reading. When the operator depresses the activation button 22 on the probe handle 20 or depresses foot pedal 52, the microprocessor 16 records how many of the sensing circuits 60 have been triggered, thus registering the amount of contact between the exterior surface of the probe tip 30 and the tissue of the periodontal pocket, thereby measuring how many millimeters of the probe tip 30 has been inserted into the periodontal pocket. The depth information may be displayed on the display 24 and/or sent to the computer 50.

FIG. 12 illustrates a further example of a periodontal probe tip 30 having a resistance touch reader 40b configured in a slightly different manner. In this example, the outside surface of probe tip 30 is divided into wide conductive bands 64 and narrow conductive bands 66, that function as the electrodes 64, 66 in the resistance touch sensing circuit 60 of resistance touch sensor 14b. The two conductive bands/electrodes 64 and 66 are separated by an insulated, non-conducting gap 65. Wires 36 connect each pair of electrodes 64, 66 to resistance touch sensor 14b. A second insulating gap 65' separates each pair of electrodes 64, 66 from the next adjacent pair of electrodes 64, 66. When the probe tip 30 is inserted into the periodontal pocket, the surrounding tissue will come in contact with the outside surface of the probe tip 30. If the tissue bridges the insulated gap 65 between the first pair of conductive bands 64, 66, the corresponding resistance touch sensing circuit 60 will record a positive reading. If the tissue bridges the next insulated gap 65 between the next pair of conductive bands 64, 66, a second sensing circuit 60 will record a positive reading. When the operator depresses the activation button 22 on the probe handle 20 or depresses foot pedal 52, the microprocessor 16 records how many of the sensing circuits 60 have been triggered, thus registering the amount of contact between the exterior surface of the probe tip 30 and the tissue of the periodontal pocket, thereby measuring the depth to which the probe tip 30 has been inserted into the periodontal pocket. The depth information may be displayed on the display 24 and/or sent to the computer 50.

Figure 13:
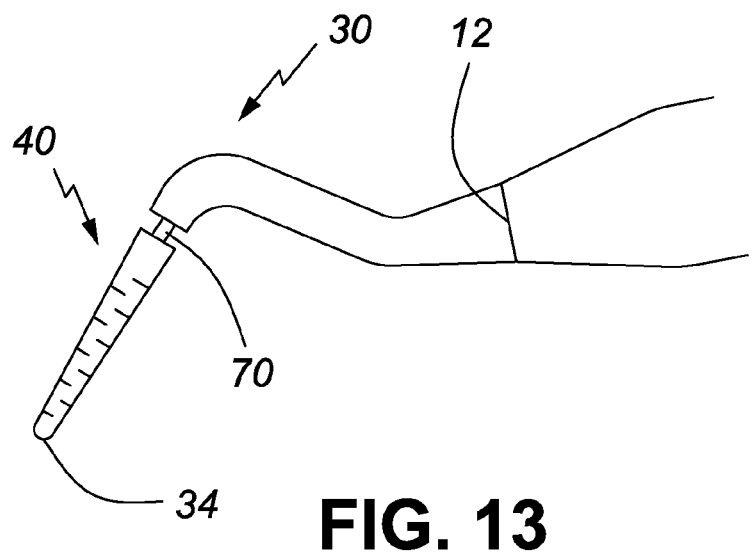
FIG. 13 shows a periodontal probe tip having a pressure sensitive switch for activating the periodontal probe to take a reading.
Figure 14:
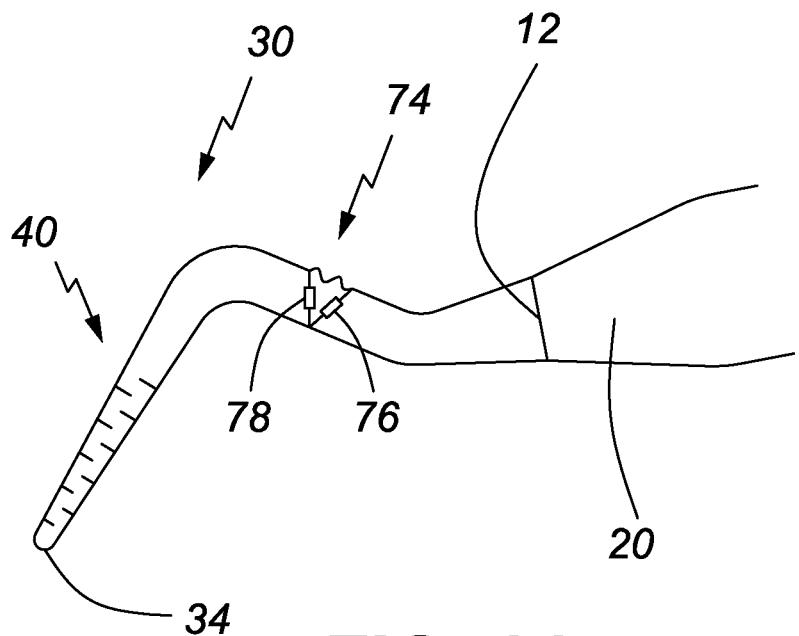
FIG. 14 shows a periodontal probe tip having a flex switch for activating the periodontal probe to take a reading
Figure 15:
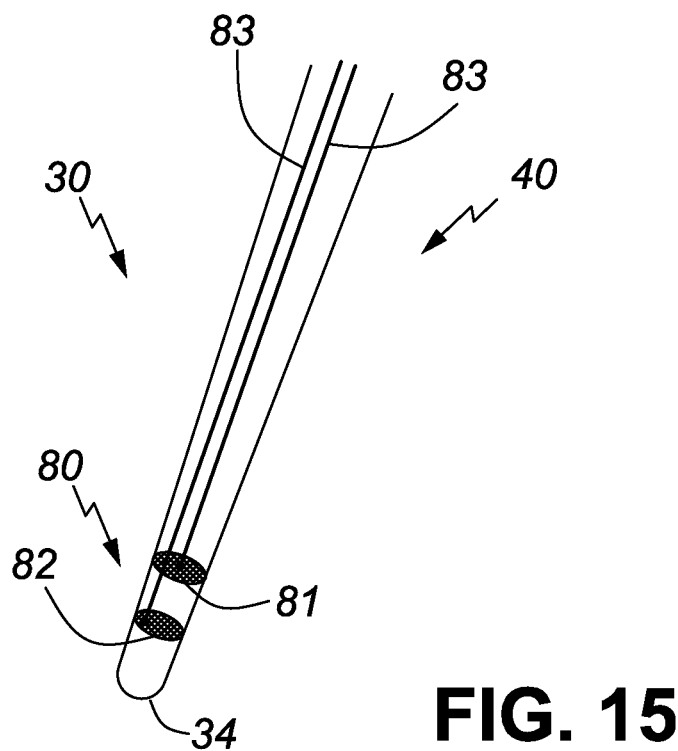
FIG. 15 shows a cutaway side view of a periodontal probe tip having a resistive switch mechanism at the tip end for activating the periodontal probe to take a reading.

Two methods for activation of the periodontal probe 10 to record a reading have been described. One is by pressing the activation button 22 on the probe handle 20, and the second is by depressing the foot pedal 52 attached to computer 50. The skilled reader will appreciate that there are numerous other possibilities for activation of the periodontal probe 10 to take a reading. In one example (not shown), voice recognition circuits could be included on the probe 10 or attached to computer 50, which would permit the user to activate the probe using voice commands. In another example, shown in FIG. 13, probe tip 30 may be fitted with a pressure sensitive switch or sensor 70, which activates when tip end 34 comes in contact with the base of the periodontal pocket. Triggering of the pressure switch or sensor 70 will automatically activate the probe's touch sensor 14 causing it to send the current readings to the microprocessor 16. In a further example, shown in FIG. 14, a flexible pressure switch or sensor 74 may be used on the probe tip 30. In this case, once the tip end 34 comes in contact with the base of the periodontal pocket, the probe tip 30 will flex, bringing switch plates 76 and 78 into contact to complete the circuit and trigger the switch/sensor 74. Activation of flex switch/sensor 74 will automatically activate the probe's touch sensor 14 causing it to send readings to the microprocessor 16. Yet another example is shown in FIG. 15. In this example, probe tip 30 is provided with a resistive switch or sensor mechanism 80 at the tip end 34. Resistive switch/sensor 80 consists of two wire mesh plates 81 and 82. When tip end 34 comes in contact with the base of the periodontal pocket, pressure is applied causing the two palates 81 and 82 to come into contact, triggering the switch/sensor 80 and automatically activating the probe's touch sensor 14, causing it to send readings to the microprocessor 16.

Pressure switch/sensor 70, flex switch/sensor 74, and resistive switch/sensor 80 may have adjustable pressure threshold settings to suit the comfort needs of the patient. Each switch or sensor can be set to activate at specified pressure settings, which can be stored in the microprocessor 16 or the computer 50 for each patient. The pressure settings may be set to different threshold levels based on standardize averages for healthy versus diseased tissue.

Figure 16:
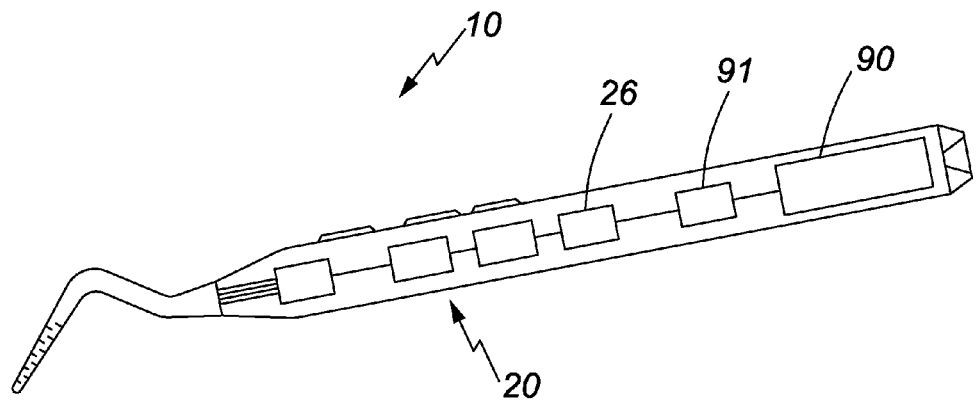
FIG. 16 shows a partial cutaway side view of a periodontal probe equipped with a thermo electric coupler (TEC) for powering the probe.
Figure 17:
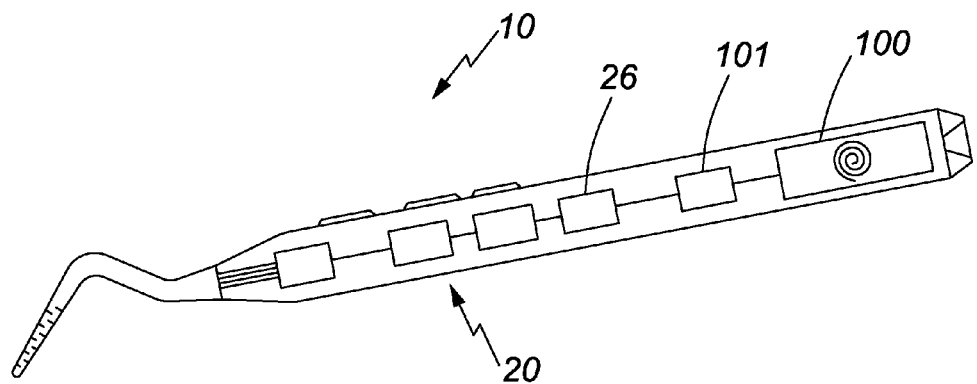
FIG. 17 shows a cutaway side view of a periodontal probe equipped with a power transfer coil (PTC) for powering the probe

Two options have been discussed for powering the periodontal probe 10. One option is to use a rechargeable battery 26 located in the handle 20 as shown in FIG. 1. Another option is to directly power the probe using a wired connection 28 to the computer 50 as shown in FIG. 2. Two other options are shown in FIGS. 16 and 17. FIG. 16, shows a thermo electric coupler (TEC) 90 and TEC controller 91 located in the handle 20. TEC 90 is used to generate electricity to charge battery 26 when the probe is heated up and cooled down during the sterilization process. Electricity is generated by the TEC 90 whenever there is a temperature difference between the inside and outside of the probe handle 20. Such temperature differences are created whenever the probe is placed into or removed from an autoclave for sterilization.

FIG. 17, shows a power transfer coil (PTC) 100 and PTC controller 101 located in the handle 20. PTC 100 generates electricity to charge battery 26 whenever it is placed in close proximity to another energized power transfer coil. This could take place when the probe is swiped for RFID identification, or the probe could be stored next to an energized PTC.

Of course, the reader will appreciate that other options are available for powering and charging the probe 10, such as using a solar panel to charge the battery 26, or to use a vibration generator such as the type found in wristwatches. In addition, combinations of the above-mentioned power generation and supply techniques may be used.

The inventors anticipate that there will be multiple periodontal probes 10 in use in a single dental office, all attached or communicating wirelessly with a single computer 50. In a wireless environment, there is the problem of identifying which probe is being used. One solution is to embed a radio frequency identification (RFID) chip into the handle 20 of each probe 10. The chip can be swiped over an RFID reader attached to computer 50 to identify which probe is being used. In a situation where there are one or more probes 10 and multiple computers 50, an RFID reader can be embedded in the handle 20 of each probe 10 and an RFID chip can be attached to each computer 50. In this situation, the probe handle would be swiped against the RFID chip on the desired computer to identify which computer is being used. Of course, one skilled in the art will understand that numerous other methods of verification are possible. For example, one or two dimensional bar codes and bar code readers could be employed. In the alternative, software could be used on the wireless transmitter/receiver 18 to send identification codes to the computer 50 to identify which of the probes is being used.

The previous detailed description is provided to enable any person skilled in the art to make or use the present periodontal probe. Various modifications to those embodiments will be readily apparent to those skilled in the art, and the generic principles defined herein may be applied to other embodiments without departing from the scope of the periodontal probe as defined by the appended claims. Thus, the present periodontal probe is not intended to be limited to the embodiments shown herein, but is to be accorded the full scope consistent with the appended claims, wherein reference to an element in the singular, such as by use of the article "a" or "an" is not intended to mean "one and only one" unless specifically so stated, but rather "one or more". All structural and functional equivalents to the elements of the various embodiments described throughout the disclosure that are known or later come to be known to those of ordinary skill in the art are intended to be encompassed by the elements of the claims. Moreover, nothing disclosed herein is intended to be dedicated to the public regardless of whether such disclosure is explicitly recited in the claims.

The invention claimed is:

1. A periodontal probe for measuring a depth of a periodontal pocket, the periodontal probe comprising:
   a handle;
   a probe tip having a proximal end connected to the handle and an opposite distal end for insertion into the periodontal pocket, the probe tip including multiple capacitive touch sensitive readers located on an exterior surface of the probe tip for measuring contact between the exterior surface of the probe tip and tissue of the periodontal pocket, each capacitive touch sensitive reader comprising an electrically conductive band or ring arranged around a circumference of the probe tip;
   a corresponding capacitive touch sensor connected to the capacitive touch sensitive readers for measuring contact between the electrically conductive bands or rings on the probe tip and the tissue of the periodontal pocket; and
   a microcontroller connected to the capacitive touch sensor, wherein the depth of the periodontal pocket is determined by a number of electrically conductive bands or rings for which a capacitance reading generated by the corresponding capacitive touch sensor increases above a predetermined threshold capacitance as a result of the contact between the exterior surface of the probe tip and the tissue of the periodontal pocket.

2. The periodontal probe as defined in claim 1, wherein the touch sensitive readers are positioned at selected incremental distances from the distal end of the probe tip.

3. The periodontal probe as defined in claim 1, further including at least one additional capacitive touch sensitive reader connected to a separate corresponding touch sensor, the at least one additional capacitive touch sensitive reader comprising an electrically conductive strip oriented longitudinally on the exterior surface of the probe tip, wherein the at least one electrically conductive strip is electrically insulated from the electrically conductive bands or rings.

4. The periodontal probe as defined in claim 1, including an activation switch for activating the periodontal probe to make a reading of the depth of the periodontal pocket once the distal end of the probe tip makes contact with a bottom of the periodontal pocket.

5. The periodontal probe as defined in claim 4, wherein the activation switch is a pressure sensitive sensor located on the probe tip to automatically activate the periodontal probe to make a reading of the depth of the periodontal pocket once the distal end of the probe tip makes contact with a bottom of the periodontal pocket.

6. The periodontal probe as defined in claim 1, including a rechargeable battery for providing electric power to operate the periodontal probe, and a thermo electric coupler for generating electricity to re-charge the battery when the periodontal probe is heated or cooled.

7. The periodontal probe as defined in claim 1, including a rechargeable battery for providing electric power to operate the periodontal probe, and a power transfer coil for generating electricity to re-charge the battery.

8. The periodontal probe as defined claim 1, including a means for individually identifying the periodontal probe in situations where multiple periodontal probes are being used in close proximity.

* * * * *